United States Patent [19]

Remy et al.

[11] 4,020,169

[45] Apr. 26, 1977

[54] PROCESS FOR PREPARING ARYL TRIFLUOROMETHYLSULFIDES

[75] Inventors: David C. Remy, North Wales; Mark B. Freedman, Glenside, both of Pa.

[73] Assignee: Merck & Co., Inc., Rahway, N.J.

[22] Filed: Dec. 22, 1975

[21] Appl. No.: 642,865

[52] U.S. Cl. .................. 260/328; 260/294.8 R; 260/470; 260/577; 260/586 F; 260/609 R
[51] Int. Cl.$^2$ ............... C07D 335/16; C07C 148/00
[58] Field of Search .......... 260/328, 586 F, 609 R, 260/294.8 R, 470, 577

[56] References Cited

OTHER PUBLICATIONS

Yagupolskii, et al., Synthesis, 721 (11–75).

*Primary Examiner*—Cecilia M. S. Jaisle
*Attorney, Agent, or Firm*—William H. Nicholson; Harry E. Westlake, Jr.

[57] ABSTRACT

Trifluoromethylthiocopper, formed in situ by the reaction of bis-(trifluoromethylthio)mercury with copper, reacts with aromatic bromides and iodides to give aryl trifluoromethyl sulfides.

8 Claims, No Drawings

PROCESS FOR PREPARING ARYL TRIFLUOROMETHYLSULFIDES

BACKGROUND OF THE INVENTION

The trifluoromethylthio and trifluoromethylsulfonyl groups are important nuclear substituents in the preparation of potential new dyes, medicinal agents, fungicides, insecticides, and solvents. At present, there are two standard procedures for the introduction of a trifluoromethylthio group into an aromatic nucleus. The first method requires a photoinitiated chlorination of an aryl methyl sulfide side chain, followed by reaction with antimony trifluoride (Eq. 1). O. Scherer, *Angewante Chem.*, 52, 457 (1939); French Pat. No. 820,796 (1937).

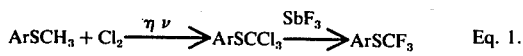

Eq. 1.

The second method uses trifluoromethanesulfenyl chloride in either one of two ways. In one procedure (Eq. 2), W. A. Sheppard. *J. Org. Chem.*, 29, (1964) reaction of an aryl Grignard reagent with trfluoromethanesulfenyl chloride gives the desired aryl trifluoromethyl sulfide, while in the other procedure (Eq. 3), S. Andreades et al., *J. Org. Chem.*, 29, 898 (1964), reaction of activated aromatic derivatives, such as anilines, with trifluoromethanesulfenyl chloride leads to para-substituted aryl trifluoromethyl sulfides. When higher temperatures and Lewis acid catalysts are used, less activated aryl derivatives undergo reaction, but mixtures of aryl trifluoromethyl sulfide isomers are obtained.

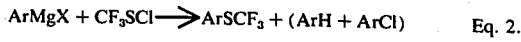

Eq. 2.

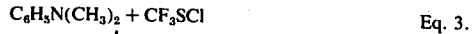

Eq. 3.

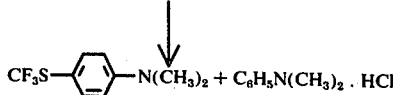

Alkyl trifluoromethyl sulfides have been prepared from the reaction of bis-(trifluoromethylthio)mercury or trifluoromethylthiosilver with alkyl iodides. Also, trifluoromethylthiosilver has been used to prepare benzyl trifluoromethylsulfides from benzyl iodides.

SUMMARY OF THE INVENTION

It has now been found that the reaction of trifluoromethylthiocopper with aryl bromides and iodides provides a convenient, one-step route to the synthesis of aryl trifluoromethyl sulfides. This procedure offers a number of advantages over existing processes, in that (1) the aromatic nucleus may contain electron-donating or electron withdrawing groups, (2) Grignard sensitive groups may be present in the molecule, (3) pure ortho, meta, and para isomers are obtained from the reaction of trifluoromethylthiocopper with the respective ortho, meta, and para aromatic bromide or iodide derivative, (4) yields of products range from good (60%) to excellent (100%), and (5) selective halide displacements are possible since aromatic iodides react at a significantly lower temperature than do aromatic bromides while aryl chlorides do not, in general, react.

DETAILED DESCRIPTION OF THE INVENTION

The novel process of this invention comprises the synthesis of an aryl trifluoromethyl sulfide (IV) by reaction of an aryl iodide or bromide (III) with trifluoromethylthiocopper (II) formed by the reaction of copper with bis(trifluoromethylthio)mercury (I).

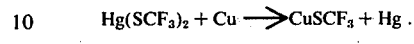

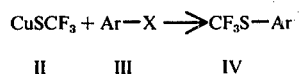

where X is iodo or bromo and Ar is aromatic. Bis(trifluoromethylthio)mercury, alone, does not react with III. The copper reagent, II, does not need to be prepared prior to the condensation reaction. Indeed, a product of comparable yield and purity is obtained when II is formed in situ during reaction.

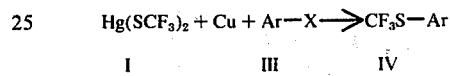

Stoichiometrically, one-half mole of I and 1 mole of copper are required for reaction with 1 mole of III and use of these proportions do provide the desired product. However, since the efficiency of the in situ preparation of II from I is not known, proportions of 0.5–8 moles and preferably 1–4 moles of I, to 1–30 moles and preferably 3.6–14.5 moles of copper, to one mole of III are used. Empirically, it has been found that a ratio of about two moles of I per mole of aryl iodide or bromide and about 3.6 moles of copper per mole of I gives good to excellent yields of products. These products are often of sufficient purity to be used directly in subsequent reactions, as for example, oxidation to the trifluoromethylsulfonyl derivatives. Both I and II are known to form very stable complexes with a variety of compounds, including amines. For this reason, where the starting material includes an amino function, an extra mole of I and an extra 3.6 moles of copper per mole of III are generally employed.

The novel process is conducted in a polar organic solvent such as dimethylformamide, quinoline or hexamethylphosphoramide, at a temperature between about 50° C. and about 200° C. Reaction times of 0.5 to 24 hours can be employed, and preferably about 1–10 hours.

The scope and utility of the reaction of aryl iodides and bromides with trifluoromethylthiocopper is illustrated in Table I. Examination of this table shows that the aromatic nucleus may contain electron withdrawing or electron donating groups. Pure ortho, meta, and parasubstituted aryl trifluoromethyl sulfides are obtained from ortho, meta, and para-substituted aryl iodides or bromides. The yield and purity of the crude, isolated products are often greater than 90%. Also, di-substitution of p-diiodobenzene occurs readily as does selective replacement of iodine in p-chloroiodobenzene.

A preferred embodiment of the novel process of this invention is the preparation of an aryl trifluoromethyl sulfide of structural formula:

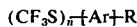

wherein [Ar] is an aromatic or heteroaromatic compound of up to 3 fused rings; R is one or more groups selected from hydrogen, chloro, fluoro, nitro, di(lower alkyl)amino, lower alkoxy, lower alkoxycarbonyl, lower alkyl, fluorolower alkyl, nitro-lower alkyl, di(-lower alkyl)amino-lower alkyl, lower alkoxy-lower alkyl and lower alkoxycarbonyllower alkyl; and $n$ is 1, 2 or 3, which comprises reacting a compound of formula:

wherein X is bromo or iodo, and Ar and R are as defined above, with trifluoromethylthiocopper in an inert polar organic solvent at 50°–200° C. for 0.5–24 hours.

A still more preferred embodiment of the novel process of this invention is the preparation of an aryl trifluoromethyl sulfide of structural formula:

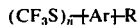

wherein [Ar] is an aromatic or heteroaromatic compound of up to 3 fused rings; R is one or more groups selected from hydrogen, chloro, fluoro, nitro, di(lower alkyl)amino, lower alkoxy, lower alkoxycarbonyl and lower alkyl, and $n$ is 1, 2 or 3, which comprises reacting a compound of formula:

wherein X is bromo or iodo, and Ar and R are as defined above, with trifluoromethylthiocopper in an inert polar organic solvent at 50°–200° C. for 0.5–24 hours.

The novel process of this invention provides trifluoromethylthio-aromatic compounds of diverse utilities. Some of the products are valuable starting materials for the synthesis of biologically active compounds. For example, p-chloro(trifluoromethylthio)benzene is useful in the synthesis of phenothiazine tranquilizers as described by Nodiff et al., *J. Org. Chem.*, 25, 60 (1960). 3-Trifluoromethylthio-5H-dibenzo[a,d]cycloheptene-5-one on treatment with 1-methyl-4-piperidyl magnesium chloride as described in U.S. Pat. No. 3,014,911 of Engelhardt provides 3-trifluoromethylthiocyproheptadine useful for the preparation of the corresponding compounds with a 10-keto or 10-hydroxy group which are antihistamines and appetite stimulants as described by Prugh in British Pat. No. 1,336,334.

Similarly, 2-(trifluoromethylthio)thioxanthen-9-one on treatment with 1-methyl-4-piperidylmagnesium chloride provides 1-methyl-4-[2-(trifluoromethylthio)-thioxanthen-9-ylidene]piperidine useful as an antipsychotic agent when administered to a patient orally at a rate of 2–200 mg/kg/day and preferably about 5–50 mg/kg/day.

4-Dimethylamino-trifluoromethylthiobenzene is useful for preparing salts with penicillin to form an antibacterial agent. Ethyl o, m, and p-trifluoromethylthiobenzoate are useful for the preparation of the corresponding benzoic acids useful as preservatives in foodstuffs.

3-Trifluoromethylthiopyridine, p-trifluoromethylthiotoluene, and p-trifluoromethylthionitrobenzene are useful solvents in organic chemistry.

GENERAL PROCEDURE INVOLVING PREFORMED TRIFLUOROMETHYLTHIOCOPPER

Preparation of ethyl-p-(trifluoromethylthio)benzoate (see Example 2 of Table)

An intimate mixture of 21.87 g. (0.0543 mol) of bis-(trifluoromethylthio)mercury and 12.53 g. (0.197 mol) of copper dust was heated at 80°–100° until development of a bright orange color. Heating was continued at 150° for 0.5 hr. After cooling, 7.50 g. (0.027 mol) of ethyl p-iodobenzoate and 30 ml. of DMF were added to the copper colored residue, and the mixture was stirred and heated at 110°–120° for 3 hr. The cooled dark reaction mixture was poured into 500 ml. of water and 200 ml. of benzene. After stirring vigorously, the mixture was filtered through Celite, and the filter cake was washed with hot benzene. The combined benzene phases were washed with water, dried MgSO$_4$), and filtered. The benzene was removed on a rotary evaporator to give 6.10 g. (90%) of ethyl-p-(trifluoromethylthio)benzoate that was 98.4% pure by glc.

GENERAL PROCEDURE FOR THE PREPARATION OF NEUTRAL ARYL TRIFLUOROMETHYL SULFIDES

Preparation of ethyl-o(trifluoromethylthio)benzoate (see Example 6 of Table

A mixture of 15.0 g. (0.0543 mol) of ethyl-o-iodobenzoate, 43.78 g. (0.1087 mol) of Hg(SCF$_3$)$_2$, 25.07 g. (0.395 mol) of copper dust, and 60 ml. of DMF was stirred and heated at 110°–120° for 1 hr. The reaction was worked up as in Example 2 to give a quantitative yield of ethyl-o-(trifluoromethylthio)benzoate that was 97.9% pure by glc. The slight yellow color of this crude product was removed by distillation, b.p. 70°–71° (0.7 mm), N$_D$$^{25}$ 1.4879.

A solution of 5.0 g. of ethyl-o-(trifluoromethylthio)-benzoate, 30 ml. of ethanol and 20 ml. of 10% sodium hydroxide was refluxed for 1.5 hrs. After cooling, the solution was acidified with 6N hydrochloric acid. The product was collected by filtration, dried, and recrystallized from a mixture of 60% hexane-40% benzene to give o-(trifluoromethylthio)benzoic acid, m.p. 119-121°.

Anal. Calcd. for C$_8$H$_5$F$_3$O$_2$S: C, 43.24; H, 2.27; F, 25.65. Found: C, 43.31; H, 2.30; F, 25.86.

GENERAL PROCEDURE FOR THE PREPARATION OF BASIC ARYL TRIFLUOROMETHYL SULFIDES

Preparation of 3-trifluoromethylthiopyridine (See Example 13 of Table)

A mixture of 5.0 g. (0.024 mol) of 3-iodopyridine, 29.48 g. (0.0732 mol) of bis-(trifluoromethylthio)mercury, 16.96 g. (0.267 mol) of copper dust and 50 ml. of DMF was stirred and heated at 110°–120° for 3 hr. After cooling in an ice bath, 100 ml. of ether and 50 ml. of 5N sodium hydroxide were added and the mixture was stirred overnight at room temperature. The mixture was filtered through Celite, and the aqueous phase was separated and extracted with two 100 ml. portions of ether. All of the ether phases were combined, washed with three 100 ml. portions of water, dried (MgSO$_4$), filtered, and the ether removed on a rotary evaporator. The yield of crude 3trifluoromethylthiopyridine was 4.15 g. (95%) that was 83.5% pure by glc. The product was purified by distillation, b.p. 150°–151°, $N_D^{25}$ 1.4676. The proton nmr (CDCl$_3$) showed three multiplets centered at δ7.42 (1H), 8.08 (1H), and 8.83 (2H), while the fluorine spectrum showed a sharp singlet at δ41.9.

Anal. Calcd. for C$_6$H$_4$F$_3$NS: C, 40.22; H, 2.25; N, 782; F, 31.82; S, 17.89. Found: C, 39.79; H, 2.42; N, 7.79; F, 31.53; S, 17.80.

Employing the appropriate procedure (neutral or basic) substantially as described in the foregoing General Procedures, but substituting for the starting materials used therein an equimolecular amount of the Starting Materials listed for Examples 1 through 14 in Table I, there are produced the corresponding Products also listed in Table I.

EXAMPLE 15

Preparation of 3-trifluoromethylthio-5H-dibenzo [a,d]-cyclohepten-5-one

A mixture of 42.56 g. of bis(trifluoromethylthio)mercury, 17.27 g. of 3-bromo-5H-dibenzo[a,d]cyclohepten-5-one, 28 g. of electrolytic copper dust, 98 ml. of quinoline and 84 ml. of pyridine is stirred and heated from 100° C. to 195° C. and held at 195° C. for 18 hours. The mixture is shaken with 400 ml. of 6N hydrochloric acid and 400 ml. benzene. The organic phase is washed with 5 × 300 ml. of 3N hydrochloric acid and 5 × 300 ml. of water, dried over magnesium sulfate, filtered and concentrated to dryness. The crystalline residue is recrystallized from 100 ml. of methanol to give 14.83 g. (78%) of 3-trifluoro-methylthio-5H-dibenzo[a,d]cyclohepten-5-one, m.p. 87°–88° C.

TABLE I

PREPARATION OF ARYL TRIFLUOROMETHYL SULFIDES

| EXAMPLE | STARTING MATERIAL | SOLVENT; REACTION TEMPERATURE, ° C.; TIME, HR. | MOLES STARTING MATERIAL/ MOLES Hg(SCF$_3$)$_2$/MOLES Cu | PRODUCT |
|---|---|---|---|---|
| 1 | p-IC$_6$H$_4$CO$_2$C$_2$H$_5$ | DMF; 110–120; 3 | 1/2/0 | None |
| 2 | p-IC$_6$H$_4$CO$_2$C$_2$H$_5$ | DMF; 110–120; 3 | 1/2/7.3$^c$ | p-CF$_3$SC$_6$H$_4$CO$_2$C$_2$H$_5$ |
| 3 | p-IC$_6$H$_4$CO$_2$C$_2$H$_5$ | DMF; 110–120; 3 | 1/2/7.3$^e$ | p-CF$_3$SC$_6$H$_4$CO$_2$C$_2$H$_5$ |
| 4 | p-IC$_6$H$_4$CO$_2$C$_2$H$_5$ | DMF; 110–120; 3 | 1/1/3.6$^e$ | p-CF$_3$SC$_6$H$_4$CO$_2$C$_2$H$_5$ |
| 5 | m-IC$_6$H$_4$CO$_2$C$_2$H$_5$ | DMF; 110–120; 2 | 1/2/7.3$^e$ | m-CF$_3$SC$_6$H$_4$CO$_2$C$_2$H$_5$$^f$ |
| 6 | o-IC$_6$H$_4$CO$_2$C$_2$H$_5$ | DMF; 110–120; 1 | 1/2/7.3$^e$ | o-CF$_3$SC$_6$H$_4$CO$_2$C$_2$H$_5$ |
| 7* | p-BrC$_6$H$_4$CO$_2$C$_2$H$_5$ | QUINOLINE; 150–190; 10 | 1/2/7.3$^e$ | p-CF$_3$SC$_6$H$_4$CO$_2$C$_2$H$_5$ |
| 8 | p-ClC$_6$H$_4$CO$_2$C$_2$H$_5$ | QUINOLINE; 238; 4 | 1/2/7.3$^e$ | None |
| 9 | p-I$_2$C$_6$H$_4$ | 1/4/14.5$^e$ | p-(CF$_3$S)$_2$C$_6$H$_4$ | |
| 10 | p-IC$_6$H$_4$NO$_2$ | DMF; 110–120; 2.5 | 1/2/7.3$^e$ | p-CF$_3$SC$_6$H$_4$NO$_2$ |
| 11 | p-IC$_6$H$_4$Cl | DMF; 110–120; 2.5 | 1/4/14.5$^e$ | p-CF$_3$SC$_6$H$_4$Cl |
| 12 | p-BrC$_6$H$_4$N(CH$_3$)$_2$ | HMPA; 160–175; 12 | 1/3/10.9$^e$ | p-CF$_3$SC$_6$H$_4$N(CH$_3$)$_2$ |
| 13 | 3-IC$_5$H$_4$N | DMF; 110–120; 3 | 1/3/10.9$^e$ | 3-CF$_3$SC$_5$H$_4$N |
| 14 | p-BrC$_6$H$_4$CH$_3$ | HMPA; 160–180; 12 | 1/2/7.3$^e$ | p-CF$_3$SC$_6$H$_4$CH$_3$ |

| EXAMPLE$^a$ | STARTING MATERIAL | % YIELD AND (% PURITY, GLC) OF ISOLATED CRUDE PRODUCT | PRODUCT B.P. ° C (mm) | PRODUCT, M.P.° C OR $N_D^{25}$ |
|---|---|---|---|---|
| 1 | p-IC$_6$H$_4$CO$_2$C$_2$H$_5$ | — | — | — |
| 2 | p-IC$_6$H$_4$CO$_2$C$_2$H$_5$ | 90 (98.4) | { 81 (0.9), 106–110 (7) }$^d$ | { 1.4845 }$^d$ |
| 3 | p-IC$_6$H$_4$CO$_2$C$_2$H$_5$ | 88 (96.7) | | |
| 4 | p-IC$_6$H$_4$CO$_2$C$_2$H$_5$ | 98.5 (84) | | |
| 5 | m-IC$_6$H$_4$CO$_2$C$_2$H$_5$ | 90 (92.5) | — | 72–74$^g$ |
| 6 | o-IC$_6$H$_4$CO$_2$C$_2$H$_5$ | 100 (97.9) | 71 (0.7) | 1.4879 |
| 7* | p-BrC$_6$H$_4$CO$_2$C$_2$H$_5$ | 100 (88.6) | — | — |
| 8 | p-ClC$_6$H$_4$CO$_2$C$_2$H$_5$ | — | — | — |
| 9 | p-I$_2$C$_6$H$_4$ | 61.5 (96.9) | 71–74 (15) | 39–42$^h$ |
| 10 | p-IC$_6$H$_4$NO$_2$ | 89 (82) | 115–122 (20)$^i$ | — |
| 11 | p-IC$_6$H$_4$Cl | 78 (100) | 173–175$^j$ | 1.4900 |
| 12 | p-BrC$_6$H$_4$N(CH$_3$)$_2$ | 100 (89.2) | 56–59 (0.10)$^k$ | 1.5269$^k$ |
| 13 | 3-IC$_5$H$_4$N | 95 (83.5) | 150–151 | 1.4676 |
| 14 | p-BrC$_6$H$_4$CH$_3$ | 79 (84.5) | 67–85 (15)$^l$ | 1.4657 |

$^a$Example number corresponds to procedure number in Experimental Section.
$^b$All compounds exhibited H$^1$ and F$^{19}$ nmr spectra consistent with the assigned structure.
$^c$Trifluoromethylthiocopper was preformed. See Experimental Section.
$^d$Lit. b.p. 96–7 (5 mm), $N_D^{25}$ 1.4812.
$^e$Trifluoromethylthiocopper was formed in situ during reaction. See Experimental Section.
$^f$Hydrolyzed by the procedure used to hydrolyze the ortho isomer; see Experimental Section, Example 6.
$^g$M.p. of 3-(trifluoromethylthio)benzoic acid. Lit. m.p. 75–6°.
$^h$Lit. m.p. 42–3°.
$^i$Lit. b.p. 119° (20 mm).
$^j$Lit b.p. 173–4°.
$^k$Lit. b.p. 54° (0.15 mm), $N_D^{25}$ 1.5309.
$^l$Lit. b.p. 80° (15 mm).

EXAMPLE 16

Preparation of 2-(trifluoromethylthio)thioxanthen-9-one

A mixture of 13.0 g. (0.0446 mol) of 2-bromothioxanthen-9-one, 30.87 g. (0.0766 mol) of bis(trifluoromethylthio)mercury, 20.36 g. (0.32 mol) of copper powder, 7 ml. of pyridine and 70 ml. of quinoline is stirred at 170°–190° for 20 hours. The solution is cooled and diluted with 200 ml. of 6N hydrochloric acid and 200 ml. of benzene. After stirring vigorously, the mixture is filtered through Filter-Cel using benzene to wash the filter cake. The aqueous acid phase is removed and the benzene phase is washed with 200 ml. of 3N hydrochloric acid and four 250 ml. portions of water. After drying over magnesium sulfate, the solution is filtered and the benzene is removed. The residue is dissolved in a small amount of benzene and chromatographed on a silica gel column (2" × 30") packed in benzene. The product is eluted with benzene to give 5.90 g. of material, which, after recrystallization from methanol, gives 5.24 gm. of 2-(trifluoromethylthio)thioxanthen-9-one, m.p. 126°–127°.

EXAMPLE 17

1-Methyl-4-[2-(trifluoromethylthio)thioxanthen-9-ylidene] piperidine

To an ice cooled solution of 5.10 g. (0.0163 mol) of 2-trifluoromethylthio)thioxanthen-9-one in 60 ml. of dry tetrahydrofuran is added dropwise 25 ml. of 0.72 M 1-methyl-4-piperidylmagnesium chloride in tetrahydrofuran. After the addition is complete, the solution is stirred at room temperature for 1 hour. The tetrahydrofuran is removed on a rotary evaporator. The red-oily residue that remains is dissolved in benzene and water is added dropwise until a clear benzene supernatant and a gelatinous aqueous phase is obtained. The benzene phase is decanted and the gelatinous aqueous phase is extracted with two 100 ml. portions of boiling benzene. The benzene phases are combined and evaporated to dryness. The residue, which crystallizes when triturated with acetonitrile, is removed by filtration and washed with acetonitrile to give 3.29 g. of 1-methyl-4-(2-trifluoromethylthio-9-hydroxythioxanthen-9-yl)piperidine.

A solution of 3.29 g. of 1-methyl-4-(2-trifluoromethylthio-9-hydroxy-thioxanthen-9-yl)piperidine in 15 ml. of trifluoroacetic anhydride and 30 ml. of trifluoroacetic acid is stirred and refluxed for 2.5 hours. The solution is evaporated to dryness. The residue is dissolved in benzene and is washed with 10% sodium hydroxide to make the free base form. The benzene is washed with water, dried over magnesium sulfate, filtered and the benzene is removed on a rotary evaporator. The residue is recrystallized from acetonitrile to give 1-methyl-4-[2-(trifluoromethylthio)thioxanthen-9-ylidene]piperidine, m.p. 104°–106° C.

Anal. Calcd. for $C_{20}H_{18}F_3NS_2$: C, 61.04 H, 4.61; N, 3.56; F, 14.49; S, 16.30. Found: C, 61.35; H, 4.74; N, 3.45; F, 14.68; S, 16.19.

What is claimed is:

1. A process for the preparation of aryl trifluoromethylsulfides which comprises reacting an aryl iodide or aryl bromide with trifluoromethylthiocopper in an inert polar organic solvent at 50°–200° C. for 0.5 to 24 hours.

2. The process of claim 1 for the preparation of an aryl trifluoromethyl sulfide of structural formula:

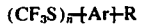

wherein [Ar] is an aromatic or heteroaromatic compound of up to 3 fused rings; R is one or more groups selected from hydrogen, chloro, fluoro, nitro, di(lower alkyl)amino, lower alkoxy, lower alkoxycarbonyl, lower alkyl, fluoro-lower alkyl, nitro lower alkyl, di(lower alkyl)aminolower alkyl, lower alkoxy-lower alkyl and lower alkoxycarbonyl-lower alkyl; and $n$ is 1, 2 or 3, which comprises reacting a compound of formula:

wherein X is bromo or iodo, and Ar and R are as defined above, with trifluoromethylthiocopper in an inert polar organic solvent at 50°–200° C. for 0.5–24 hours.

3. The process of claim 1 for the preparation of an aryl trifluoromethyl sulfide of structural formula:

wherein [Ar] is an aromatic or heteroaromatic compound of up to 3 fused rings; R is one or more groups selected from hydrogen, chloro, fluoro, nitro, di(lower alkyl) amino, lower alkoxy, lower alkoxycarbonyl and lower alkyl, and $n$ is 1, 2 or 3, which comprises reacting a compound of formula:

wherein X is bromo or iodo, and Ar and R are as defined above, with trifluoromethylthiocopper in an inert polar organic solvent at 50°–200° C. for 0.5–24 hours.

4. The process of claim 1 for the preparation of the compound of formula:

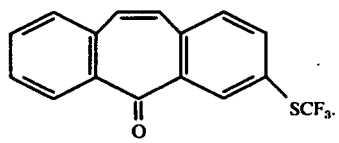

5. The process of claim 1 for the preparation of the compound of formula:

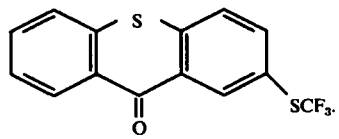

6. A process which comprises reacting an aryl halide having up to 3 halide groups selected from bromide and iodide with trifluoromethylthiocopper in an inert polar organic solvent at 50°–200° C. for 0.5 to 24 hours, whereby the halide groups are replaced by trifluoromethylthio groups.

7. The process of claim 6 wherein the aryl halide is an aromatic or heteroaromatic halide of up to 3 fused rings and is not, or is, further substituted with chloro, fluoro, nitro, di(lower alkyl)amino, lower alkoxy, lower alkoxycarbonyl, lower alkyl, fluoro-lower alkyl, nitro lower alkyl, di(lower alkyl)amino-lower alkyl, lower alkoxy-lower alkyl, or lower alkoxycarbonyl-lower alkyl.

8. The process of claim 7 wherein the aryl halide is not, or is, further substituted with chloro, fluoro, nitro, di(lower alkyl)amino, lower alkoxy, lower alkoxycarbonyl or lower alkyl.

* * * * *